(12) United States Patent
Krüger et al.

(10) Patent No.: US 6,683,029 B1
(45) Date of Patent: Jan. 27, 2004

(54) HALOPYRIMIDINES

(75) Inventors: Bernd-Wieland Krüger, Bergisch Gladbach (DE); Herbert Gayer, Monheim (DE); Peter Gerdes, Aachen (DE); Ulrich Heinemann, Leichlingen (DE); Astrid Mauler-Machnik, Leichlingen (DE); Martin Vaupel, Leichlingen (DE); Fritz Maurer, Monheim (DE); Ulrike Wachendorff-Neumann, Neuwied (DE); Gerd Hänssler, Leverkusen (DE); Karl-Heinz Kuck, Langenfeld (DE); Peter Lösel, Monheim (DE); Ralf Dunkel, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,494
(22) PCT Filed: Jun. 6, 2000
(86) PCT No.: PCT/EP00/05160
§ 371 (c)(1), (2), (4) Date: Dec. 14, 2001

(87) PCT Pub. No.: WO00/78732
PCT Pub. Date: Dec. 28, 2000

(30) Foreign Application Priority Data

Jun. 18, 1999 (DE) .......................... 199 27 914
Feb. 4, 2000 (DE) .......................... 100 05 039

(51) Int. Cl.$^7$ ........................ C07D 239/52; A01N 43/54
(52) U.S. Cl. ....................... 504/243; 544/319
(58) Field of Search ........................ 544/319; 504/243

(56) References Cited

FOREIGN PATENT DOCUMENTS

| DE | 2253624 | 9/1992 |
|----|---------|--------|
| DE | 19 646 407 | 5/1998 |
| DE | 19 723 195 | 12/1998 |
| EP | 468 684 | 1/1992 |

*Primary Examiner*—John M. Ford
(74) *Attorney, Agent, or Firm*—Richard E. L. Henderson; Joseph C. Gil

(57) ABSTRACT

The invention relates to novel halogenopyrimidines, to a plurality of processes for their preparation and to their use as pesticides.

6 Claims, No Drawings

HALOPYRIMIDINES

The invention relates to novel halogenopyrimidines, to a pluarity of processes for their preparation and to their use as pesticides.

Certain pyrimidines having a similar substitution pattern, and their fungicidal action, are already known (GB-A 2253624). However, the activity of these prior-art compounds is, in particular at low application rates and concentrations, not entirely satisfactory in all areas of use.

This invention, accordingly, provides the novel halogenopyrimidines of the general formula (I)

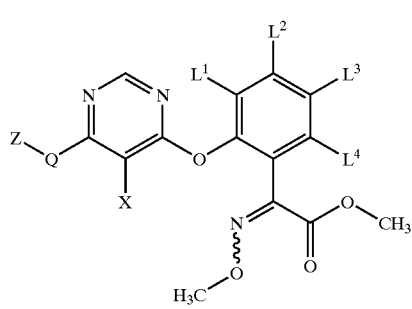

(I)

in which
- z represents in each case substituted or unsubstituted cycloalkyl, aryl or hetero-cyclyl,
- Q represents oxygen or sulphur,
- X represents halogen and
- $L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

In the definitions, the saturated or unsaturated hydrocarbon chains, such as alkyl, alkanediyl, alkenyl or alkinyl, are in each case straight-chain or branched, including in combination with heteroatoms, such as, for example, in alkoxy, alkylthio or alkylamino. Unless stated otherwise, preference is given to hydrocarbon chains having 1 to 6 carbon atoms.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen and sulphur. If the ring contains a plurality of oxygen atoms, these are not adjacent. If appropriate, the cyclic compounds form, together with other carbocyclic or heterocyclic, fused-on or bridged rings, a polycyclic ring system. Preference is given to mono- or bicyclic ring systems, in particular to mono- or bicyclic aromatic ring systems.

Cycloalkyl represents saturated carbocyclic cyclic compounds which, if appropriate, form a polycyclic ring system with other carbocyclic, fused-on or bridged rings.

A polycyclic ring system can be linked to a heterocyclic ring or a fused-on carbocyclic ring. The thus-described heterocyclyl can also be mono- or polysubstituted, preferably by methyl, ethyl or halogen. Preference is given to mono- or bicyclic ring systems, in particular to mono- or bicyclic aromatic ring systems.

Halogenoalkoxy represents partially or fully halogenated alkoxy. In the case of polyhalogenated halogenoalkoxy, the halogen atoms can be identical or different. Preferred halogen atoms are fluorine and, in particular, chlorine. If the halogenoalkoxy carries further substituents, the maximum number of halogen atoms which is possible is reduced to the remaining free valencies. Unless stated otherwise, preference is given to hydrocarbon chains having 1 to 6 carbon atoms.

Halogenoalkyl represents partially or fully halogenated alkyl. In the case of polyhalogenated halogenoalkyl, the halogen atoms can be identical or different. Preferred halogen atoms are fluorine and chlorine, in particular fluorine. If the halogenoalkyl carries other substituents, the maximum possible number of halogen atoms is reduced to the remaining free valencies. Unless stated otherwise, preference is given to hydrocarbon chains having 1 to 6 carbon atoms.

Furthermore, it has been found that the novel halogenopyrimidines of the general formula (I) are obtained when a) 2-(2-hydroxy-phenyl)-2-methoxyiminoacetates of the formula (II)

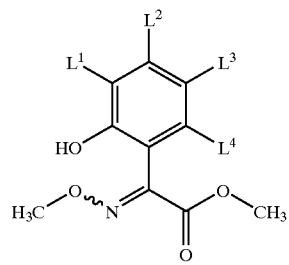

(II)

in which
$L^1$, $L^2$, $L^3$ and $L^4$ are each as defined above
are reacted with a substituted halogenopyrimidine of the general formula (III)

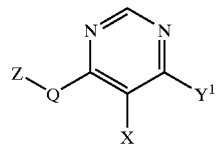

(III)

in which
Z, Q and X are each as defined above and
$Y^1$ represents halogen,
if appropriate in the presence of a diluent, if appropriate in the presence of an acid acceptor and if appropriate in the presence of a catalyst, or when b) phenoxypyrimidines of the general formula (IV)

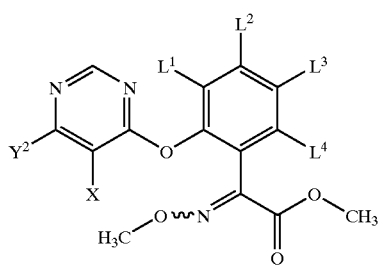

(IV)

in which
X, $L^1$, $L^2$, $L^3$ and $L^4$ are each as defined above and
$Y^2$ represents halogen are reacted with a cyclic compound of the general formula (V)

Z—Q—H     (V)

in which
Z and Q are each as defined above,
if appropriate in the presence of a diluent, if appropriate in the presence of an acid acceptor and if appropriate in the presence of a catalyst.

Finally, it has been found that the novel halogenopyrimidines of the general formula (I) have very strong activity against pests of plants.

If appropriate, the compounds according to the invention can be present as mixtures of different possible isomeric forms, in particular of stereoisomers, such as, for example, E and Z. What is claimed are both the E and the Z isomers, and any mixtures of these isomers.

The invention preferably provides compounds of the formula (I) in which
Z represents cycloalkyl having 3 to 7 carbon atoms which is in each case optionally mono- or disubstituted by halogen, alkyl or hydroxyl;
represents heterocyclyl having 3 to 7 ring members which is optionally substituted by alkyl having 1 to 4 carbon atoms or halogen;
or represents phenyl or naphthyl, each of which is optionally mono- to tetrasubstituted by identical or different substituents, where the possible substituents are preferably selected from the list below:
halogen, cyano, nitro, amino, hydroxyl, formyl, carboxyl, carbamoyl, thio-carbamoyl;
in each case straight-chain or branched alkyl, hydroxyalkyl, oxoalkyl, alkoxy, alkoxyalkyl, alkylthioalkyl, dialkoxyalkyl, alkylthio, mercaptoalkyl, alkyl-sulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl, having 1 to 6 carbon atoms in the respective hydrocarbon chains;
cycloalkyl or cycloalkyloxy having in each case 3 to 6 carbon atoms; in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, oxo, methyl, trifluoromethyl and ethyl;
or a grouping

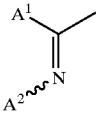

in which
$A^1$ represents hydrogen, hydroxyl or alkyl having 1 to 4 carbon atoms or cycloalkyl having 1 to 6 carbon atoms and
$A^2$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms,
and phenyl, phenoxy, phenylthio, benzoyl, benzoylethenyl, cinnamoyl, heterocyclyl or phenylalkyl, phenylalkyloxy, phenylalkylthio or heterocyclylalkyl having in each case 1 to 3 carbon atoms in the respective alkyl moieties and being in each case optionally mono- to trisubstituted in the ring moiety by halogen and/or straight-chain or branched alkyl or alkoxy having 1 to 4 carbon atoms,
Q represents oxygen or sulphur,
X represents fluorine, chlorine or bromine and
$L^1$, $L^2$, $L^3$ and $L^4$ are identical or different and independently of one another each represents hydrogen, halogen, cyano, nitro, or represents alkyl, alkoxy, alkylthio, alkylsulphinyl or alkylsulphonyl having in each case 1 to 6 carbon atoms and being in each case optionally substituted by 1 to 5 halogen atoms.

The invention relates in particular to compounds of the formula (I) in which
Z represents cyclopentyl or cyclohexyl, each of which is optionally mono- or disubstituted by fluorine, chlorine, methyl, ethyl or hydroxyl;
represents thienyl, pyridyl or furyl, each of which is optionally substituted by methyl, ethyl or chlorine;
or represents phenyl or naphthyl, each of which is optionally mono- to tetrasubstituted by identical or different substituents, where the possible substituents are preferably selected from the list below:
fluorine, chlorine, bromine, iodine, cyano, nitro, amino, hydroxyl, formyl, carboxyl, carbamoyl, thiocarbamoyl,
methyl, ethyl, n- or i-propyl, n-, i-, s- or t-butyl, 1-, 2-, 3-neo-pentyl, 1-, 2-, 3-, 4-(2-methylbutyl), 1-, 2-, 3-hexyl, 1-, 2-, 3-, 4-, 5-(2-methylpentyl), 1-2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl, methoxy, ethoxy, n- or i-propoxy, methoxymethyl, ethoxymethyl, mercaptomethyl, methylthio, ethylthio, n- or i-propylthio, methylsulphinyl, ethylsulphinyl, methylsulphonyl or ethylsulphonyl, methylthiomethyl, ethylthiomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, pentafluoropropoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl, in each case doubly attached propanediyl, ethyleneoxy, methylenedioxy, ethylenedioxy, each of which is optionally mono- to tetrasubstituted by identical or different substituents from the group consisting of fluorine, chlorine, oxo, methyl and trifluoromethyl or a grouping

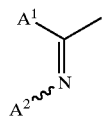

where $A^1$ represents hydrogen, methyl or hydroxyl and $A^2$ represents hydroxyl, methoxy, ethoxy, amino, methylamino, phenyl, benzyl or hydroxyethyl, and phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, 2,3-dihydro-1,4-benzodioxin-6-yl, benzodioxol-4-yl, each of which is optionally mono- to tetrasubstituted in the ring moiety by halogen and/or straight-chain or branched alkyl or alkoxy having 1 to 4 carbon atoms, Q represents oxygen, X represents fluorine and $L^1$, $L^2$, $L^3$ and $L^4$ are identical or different and independently of one another each represents hydrogen, methyl, ethyl, n- or i-propyl, n-, i-, s- or t-butyl.

In a preferred group of compounds of the formula (I), Z represents optionally substituted phenyl, naphthyl or pyridyl.

In a very particularly preferred group of compounds of the formula (I), Z represents substituted phenyl, where the possible substituents are preferably those mentioned in the preferred ranges above.

Particular preference is given to compounds of the formula (I) in which Q represents oxygen.

Particular preference is given to compounds of the formula (I) in which Z represents optionally substituted phenyl, where the substituents are preferably selected from the list below: halogen, cyano, in each case straight-chain or branched alkyl, alkylthio, alkylthioalkyl, halogenoalkyl, halogenothioalkyl.

Particular preference is given to compounds of the formula (I) in which X is fluorine.

In a further very particularly preferred group of compounds $L^1$, $L^2$ and $L^3$ each represent hydrogen and $L^4$ represents hydrogen or represents methyl.

The abovementioned general or preferred radical definitions apply both to the end products of the formula (I) and, correspondingly, to the starting materials or intermediates required in each case for the preparation.

The radical definitions given in the respective combinations or preferred combinations of radicals specifically for these radicals are, independently of the combination given in each case, also replaced by any radical definitions of other preferred ranges.

The formula (II) provides a general definition of the 2-(2-hydroxy-phenyl)-2-methoxyiminoacetates required as starting materials for carrying out the process a) according to the invention. In this formula (II), $L^1$, $L^2$, $L^3$ and $L^4$ each preferably or in particular have those meanings which have already been given in connection with the description of the compounds of the formula (I) according to the invention as being preferred or as being particularly preferred for $L^1$, $L^2$, $L^3$ and $L^4$.

The starting materials of the formula (II) are known and can be prepared by known processes (compare, for example, WO-A 94-05626, GB-A 2249092).

The formula (III) provides a general definition of the halogenopyrimidines furthermore required as starting materials for carrying out the process a) according to the invention. In this formula (III), Z, Q and X each preferably or in particular have those meanings which have already been given in connection with the description of the compounds of the formula (I) according to the invention as being preferred or as being particularly preferred for Z, Q and X. $Y^1$ represents halogen, preferably fluorine or chlorine.

The starting materials of the formula (III) are known and/or can be prepared by known methods (compare, for example, DE-A 4340181; Chem. Ber., 90 <1957> 942, 951).

The formula (IV) provides a general definition of the phenoxypyrimidines required as starting materials for carrying out the process b) according to the invention. In this formula (IV), X, $L^1$, $L^2$, $L^3$ and $L^4$ each preferably or in particular have those meanings which have already been given in connection with the description of the compounds of the formula (I) according to the invention as being preferred or as being particularly preferred for X, $L^1$, $L^2$, $L^3$ and $L^4$. $Y^2$ represents halogen, preferably fluorine or chlorine.

The starting materials of the formula (IV) are novel and also form part of the subject-matter of the present application. They are important intermediates, for example and preferably for preparing pesticides.

The phenoxypyrimidines of the general formula (IV) are obtained (Process b-1) when 2-(2-hydroxy-phenyl)-2-methoxyimino-acetates of the formula (II) are reacted with a trihalogenopyrimidine of the general formula (VI)

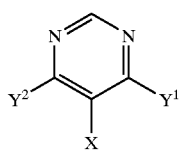

(VI)

in which

X, $Y^1$ and y2 are identical or different and each represents halogen, if appropriate in the presence of a diluent, if appropriate in the presence of an acid acceptor and if appropriate in the presence of a catalyst.

The hydroxy compounds of the formula (II) required as starting materials for carrying out the process b-1) according to the invention have already been described in connection with the description of the process a) according to the invention.

The formula (VI) provides a general definition of the trihalogenopyrimidines furthermore required as starting materials for carrying out the process b-1) according to the invention. In this formula (VI), X, $Y^1$ and $Y^2$ each represent halogen, preferably fluorine or chlorine.

The trihalogenopyrimidines are known and/or can be prepared by known methods (compare, for example, Chesterfield et al., J. Chem. Soc., 1955; 3478, 3480; WO-A 97-27189).

The formula (V) provides a general definition of the cyclic compounds furthermore required as starting materials for carrying out process b) according to the invention. In this formula (V), Z and Q each preferably or in particular have those meanings which have already been given in connection with the description of the compounds of the formula (I) according to the invention as being preferred or as being particularly preferred for Z and Q.

The cyclic compounds of the formula (V) are known chemicals for synthesis or can be prepared by simple methods.

Suitable diluents for carrying out the processes a), b) and b-1) according to the invention are all inert organic solvents. These include, by way of example and by way of preference, ethers, such as, for example, diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as, for example, acetonitrile, propionitrile, n- or i-butyronitrile or benzonitrile; amides, such as, for example, N,N-dimethylformamide, N,N-dimethylacetamide, N-methylformanilide, N-methylpyrrolidone or hexamethylphosphoric triamide; sulphoxides, such as, for example, dimethyl sulphoxide; or sulphones, such as, for example, sulpholane.

If appropriate, the processes a), b) and b-1) according to the invention are carried out in the presence of a suitable acid acceptor. Suitable acid acceptors are all customary inorganic or organic bases. These include, by way of example and by way of preference, alkaline earth metal and alkali metal hydrides, hydroxides, alkoxides, carbonates or bicarbonates, such as, for example, sodium hydride, sodium amide, potassium tert-butoxide, sodium hydroxide, potassium hydroxide, sodium carbonate, potassium carbonate, potassium bicarbonate and sodium bicarbonate.

Suitable catalysts for the processes a), b) and b-1) according to the invention are all copper(I) salts, such as, for example, copper(I) chloride, copper(I) bromide or copper(I) iodide.

When carrying out the processes a), b) and b-1) according to the invention, the reaction temperatures can be varied within a relatively wide range. In general, the processes are carried out at temperatures from −20° C. to 100° C., preferably at temperatures from −10° C. to 80° C.

For carrying out the process a) according to the invention for preparing the compounds of the formula (I), generally 0.5 to 15 mol, preferably 0.8 to 8 mol, of substituted halogenopyrimidine of the formula (III) are employed per mole of the 2-(2-hydroxy-phenyl)-2-methoxyimino-acetate of the formula (II).

For carrying out the process b) according to the invention for preparing the compounds of the formula (I), generally 0.5 to 15 mol, preferably 0.8 to 8 mol, of a cyclic compound of the general formula (V) are employed per mole of the phenoxypyrimidine of the formula (IV).

For carrying out the process b-1) according to the invention for preparing the compounds of the formula (IV), generally 1 to 15 mol, preferably 2 to 8 mol, of a trihalogenopyrimidine of the general formula (VI) are employed per mole of the 2-(2-hydroxy-phenyl)-2-methoxyimino-acetate of the formula (II).

All processes according to the invention are generally carried out under atmospheric pressure. However, it is also possible to operate under elevated or reduced pressure—in general between 0.1 bar and 10 bar.

The practice of the reaction and the work-up and isolation of the reaction products is carried out by generally customary processes (compare also the Preparation Examples).

Biology

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for exanple, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culnorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Altemaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds according to the invention can be employed particularly successfully for controlling cereal diseases, such as, for example, against Leptosphaeria species, diseases in viticulture, fruit and vegetable growing, such as, for example, against Venturia, Sphaerotheca, Phytophtora and Plasmopara species, or rice diseases, such as for example, against Pyricularia species.

Furthermore, the active compounds according to the invention may also be employed to increase the yield of crops. Moreover, they have reduced toxicity and are tolerated well by plants.

If appropriate, the active compounds according to the invention can, in certain concentrations and application rates, also be used as herbicides, for influencing plant growth and for controlling animal pests. If appropriate, they can also be used as intermediates and precursors for synthesizing other active compounds.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ for example organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

A mixture with other known active compounds, such as herbicides, or with fertilizers and growth regulators, is also possible.

In addition, the compounds of the formula (I) according to the invention also have very good antimycotic action. They have a very broad antimycotic activity spectrum, in particular against dermatophytes and yeasts, moulds and diphasic fungi (for example against Candida species such as *Candida albicans, Candida glabrata*), against Epidermophyton species, such as *Epidermophyton floccosum*, Aspergillus species, such as *Aspergillus niger* and *Aspergillus fumigatus*, Trichophyton species, such as *Trichophyton mentagrophytes*, Microsporon species, such as *Microsporon canis* and *audouinii*. The list of these fungi constitutes by no means a limitation of the mycotic spectrum that can be covered, but only has illustrative character.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, and the like. Furthermore, it is possible to apply the active compounds by the ultra-low-volume method, or to inject the active compound preparation or the active compound itself into the soil. It is also possible to treat the plant seed.

When using the active compounds according to the invention as fungicides, the application rates can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus*, Gryllotalpa spp., *Locusta migratoria migratorioides*, Melanoplus spp. and *Schistocerca gregaria*.

From the order of the Blattaria, for example, *Blatta orientalis, Periplaneta americana, Leucophaea maderae, Blattella germanica*.

From the order of the Dermaptera, for example, *Forficula auricularia*.

From the order of the Isoptera, for example, Reticulitermes spp.

From the order of the Phthiraptera, for example, *Pediculus humanus corpons*, Haematopinus spp., Linognathus spp., Trichodectes spp. and Damalinia spp.

From the order of the Thysanoptera, for example, *Hercinothrips femoralis, Thrips tabaci, Thrips palmi* and *Frankliniella accidentalis*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Mamestra brassicae, Panolis flammea*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana*, Cnaphalocerus spp.

From the order of the Coleoptera, for example, Anobium punctatum, *Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon soistitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa*, Hylemyia spp. and Liriomyza spp.

From the order of the Siphonaptera, for example, *Xenopsylla cheopis* and Ceratophyllus spp.

From the order of the Arachnida, for example, *Scorpio maurus, Latrodectus mactans, Acarus siro*, Argas spp., Omithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Hemitarsonemus spp., Brevipalpus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp., Bursaphelenchus spp.

They can be deployed with particular success to combat plant-harming insects, such as against, for example, the caterpillars of the diamondback moth (*Plutella maculipennis*).

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable Solid Carriers are for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example to widen the activity spectrum or to prevent the build-up of resistance. In many cases, synergistic effects are obtained, i.e. the activity of the mixture is greater than the activity of the individual components.

Examples of particularly advantageous co-components are the following compounds:

Fungicides aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, Rhalide, fuberidazole, furalaxyl, furametpyr, furcarbonil, furconazole, furconazole-cis, furrmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinoxyfen, sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlotophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl4-[(3-methylbenzoyl)-oxy]-2,5-thiophenedicarboxylate, cis-1-(4-chlorophenyl)-2-(1 H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl[(4-chlorophenyl)-azo]-cyanoacetate, potassium bicarbonate, methanetetrathiol-sodium salt, methyl1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine sodium salt, O,O-diethyl[2-(dipropylamino)-2-oxoethyl]-ethylphosphoramidothioate, O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides bronopol, dichlorophen, nitrapyrin, nickel dimethyldithiocarbarnate, kasugamycin, octhilinone, furancarboxylic acid, oxytetracyclin, probenazole, streptomycin, tecloftalam, copper sulphate and other copper preparations.

Insecticides/Acaricides/Nematicides abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1 H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The preparation and the use of the active compounds according to the invention is demonstrated by the examples below.

The examples below serve to illustrate the invention. However, the invention is not limited to the examples.

Preparation Examples

Example 1

Methyl 2-{2-[6-(3-fluorophenoxy)-5-fluoro-pyrimidin-4-yloxy]-phenyl}-2-methoxyiminoacetate Process a)

With cooling, 4 g (0.0287 mol) of potassium carbonate are added to a mixture of 4.6 g (0.0221 mol) of methyl 2-(2-hydroxyphenyl)-2-methoxyiminoacetate and 5 g (0.0221 mol) of 4-(3-fluorophenoxy)-5,6-difluoropyrimidine in 50 ml of acetonitrile, and the mixture is stirred at 25° C. for 12 hours. The reaction mixture is poured into 400 ml of water and extracted three times with in each case 150 ml of ethyl acetate, the organic phase is dried over sodium sulphate and the solvent is distilled off under reduced pressure. The residue is stirred with diisopropyl ether and the resulting solid is filtered off and dried. This gives 7.3 g (79.5% of theory) of methyl 2-{2-[6-(3-fluorophenoxy)-5-fluoro-pyrimidin-4-yloxy]-phenyl}-2-methoxyiminoacetate.

HPLC: logP=3.46

The compounds of the formula (I-a) mentioned in Table 1 below are obtained analogously to Example 1, and in accordance with the specifications given in the general description of the process.

TABLE 1

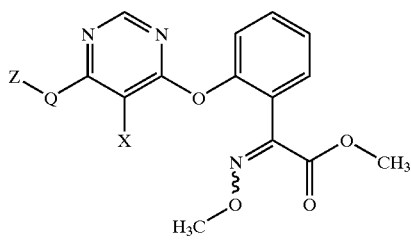

(I-a)

| Ex. No. | Q | X | Z | logP* |
|---|---|---|---|---|
| 2 | O | F | 2-chlorophenyl | 3.6 |
| 3 | O | F | 2,4-dimethylphenyl | 3.99 |
| 4 | O | F | 2-fluorophenyl | 3.40 |
| 5 | O | F | 2,5-dimethylphenyl | 3.97 |
| 6 | O | F | 2-difluoromethoxyphenyl | 3.54 |
| 7 | O | F | 2,3-dimethylphenyl | 3.88 |
| 8 | O | F | 2,3-dichlorophenyl | 4.05 |
| 9 | O | F | phenyl | 3.33 |
| 10 | O | F | 2,5-dichlorophenyl | 4.12 |
| 11 | O | F | 3-chloro-2-methylphenyl | 4.12 |
| 12 | O | F | 2-cyanophenyl | 3.07 |
| 13 | O | F | 2-bromophenyl | 3.66 |
| 14 | O | F | 2-ethylthiophenyl | 3.86 |
| 15 | O | F | 2-propylphenyl | 4.26 |
| 16 | O | F | 2-ethylthiomethylphenyl | 3.97 |
| 17 | O | F | 2-methylphenyl | 3.62 |
| 18 | O | F | 3-trifluoromethylphenyl | 4.04 |
| 19 | O | F | 3-bromophenyl | 3.96 |
| 20 | O | F | 3-cyanophenyl | 3.23 |
| 21 | O | F | 2,3-dimethoxyphenyl | 3.40 |
| 22 | O | F | 2-isopropoxyphenyl | 3.89 |
| 23 | O | F | 2-iodophenyl | 3.84 |
| 24 | O | F | 2-nitro-3-methylphenyl | 3.60 |
| 25 | O | F | 3-dimethylaminophenyl | 3.57 |
| 26 | O | F | 2-methyl-3-nitrophenyl | 3.62 |
| 27 | O | F | 2,4-difluorophenyl | 3.62 |
| 28 | O | F | 3,4-difluorophenyl | 3.67 |
| 29 | O | F | 4-cyanophenyl | 3.19 |
| 30 | O | F | 2-methoxyphenyl | 3.37 |
| 31 | O | F | 3-methoxyphenyl | 3.47 |
| 32 | O | F | 2-ethylphenyl | 4.02 |
| 33 | O | F | 2-ethoxyphenyl | 3.67 |
| 34 | O | F | 3-tert-butylphenyl | 4.65 |
| 35 | O | F | 4-trifluoromethoxyphenyl | 4.18 |
| 36 | O | F | 2-methyl-4-trifluoromethoxyphenyl | 4.43 |
| 37 | O | F | 2-methoxy-4-trifluoro-methoxyphenyl | 4.18 |
| 38 | O | F | 4-trifluoromethylthiophenyl | 4.45 |
| 39 | O | F | 6-chloro-pyrid-2-yl | 3.25 |
| 40 | O | F | 6-methyl-pyrid-2-yl | 2.95 |
| 41 | O | F | 6-methyl-pyrid-3-yl | 2.37 |
| 42 | O | F | 2-chloro-4-trifluoromethylphenyl | 4.41 |
| 43 | O | F | 2-nitro-3-chlorophenyl | 3.71 |
| 44 | O | F | 2-(2-methyl-allyl)phenyl | 4.04 |
| 45 | O | F | 3-ethylphenyl | 4.12 |
| 46 | O | F | 2-(1,1,2,3,3-penta-fluoropropoxy)phenyl | 4.14 |
| 47 | O | F | 3-trifluoromethoxyphenyl | 4.18 |
| 48 | O | F | 2-benzylthiophenyl | 4.43 |
| 49 | O | F | 2-chloro-4-trifluoromethoxyphenyl | 4.51 |
| 50 | O | F | 2-chloro-4-methoxyphenyl | 3.77 |
| 51 | O | F | 2-chloro-5-methoxyphenyl | 4.04 |
| 52 | O | F | 3-chloro-5-methylphenyl | 4.27 |
| 53 | O | F | 3-methyl-4-methylthiophenyl | 4.14 |
| 54 | O | F | 4-bromo-2-methylphenyl | 4.29 |
| 55 | O | F | 2-allyl-6-chlorophenyl | 4.35 |
| 56 | O | F | 2,3,5,6-tetrafluorophenyl | 3.94 |
| 57 | O | F | 4-methylthiophenyl | 3.81 |
| 58 | O | F | 5-chloro-2-methylphenyl | 4.18 |
| 59 | O | F | 3,5-dimethylphenyl | 4.10 |
| 60 | O | F | 2,6-dibromophenyl | 4.12 |

TABLE 1-continued (I-a)

[Structure of formula (I-a): a pyrimidine ring with Z-Q substituent, X substituent, linked via O to a phenyl ring bearing a =N-OCH₃ / C(=O)OCH₃ methoxyiminoacetate group]

| Ex. No. | Q | X | Z | logP* |
|---------|---|---|---|-------|
| 61 | O | F | 2-allyl-5-methylphenyl | 4.35 |
| 62 | O | F | 4-chloro-3-methylphenyl | 4.27 |
| 63 | O | F | 2-chloro-4-methylphenyl | 4.06 |
| 64 | O | F | 3,4-dichlorophenyl | 4.33 |
| 65 | O | F | 2-naphthyl | 4.00 |
| 66 | O | F | 2-allyloxyphenyl | 3.69 |
| 67 | O | F | 2-tert-butylphenyl | 4.47 |
| 68 | O | F | 3-chloro-2-cyanophenyl | |
| 69 | O | F | 2-trifluoromethylphenyl | |
| 70 | O | F | 2-trifluoromethoxyphenyl | |
| 71 | O | F | 2-nitrophenyl | |
| 72 | O | F | 2-mercaptomethylphenyl | |
| 73 | O | F | 3-(phenoxy)phenyl | |
| 74 | O | F | 3-methylphenyl | |
| 75 | O | F | 3-nitrophenyl | |
| 76 | O | F | 3-methyliminomethylphenyl | |
| 77 | O | F | 2-fluoro-3-trifluoromethylphenyl | |
| 78 | O | F | 3-pyridyl | |
| 79 | O | F | 4-fluorophenyl | |
| 80 | O | F | 2,2,3,3-tetrafluoro-2,3-dihydro-1,4-benzodioxin-6-yl | |
| 81 | O | F | 3,4-dimethoxyphenyl | |
| 82 | O | F | 2-chloro-4-fluorophenyl | |
| 83 | O | F | 2-chloro-3-trifluoromethylphenyl | |
| 84 | O | F | 2,3-difluorophenyl | |
| 85 | O | F | 2-cyano-6-methoxyphenyl | |
| 86 | O | F | 2-cyano-3-methoxyphenyl | |
| 87 | O | F | 5-chloro-2-cyanophenyl | |
| 88 | O | F | 6-bromo-2-cyanophenyl | |
| 89 | O | F | 2-cyano-3-fluorophenyl | |
| 90 | O | F | 4-chloro-2-cyanophenyl | |
| 91 | O | F | 2,2,3,3-tetrafluoro-2,3-dihydro-1,4-benzodioxin-5-yl | |
| 92 | O | F | 2,2-difluoro-1,3-benzodioxol-4-yl | |
| 93 | O | F | 2-ethoxymethylphenyl | |
| 94 | O | F | 2-methoxymethylphenyl | |
| 95 | O | F | 2-chloro-3-formylphenyl | |
| 96 | O | F | 2-cyano-3-methylphenyl | |
| 97 | O | F | 2-cyano-3-trifluoromethoxyphenyl | |
| 98 | O | F | 2-cyano-3-difluoromethoxyphenyl | |
| 99 | O | F | 3-cyano-2-methylphenyl | |
| 100 | O | F | 3-chloro-2-trifluoromethoxyphenyl | |
| 101 | O | F | 3-fluoro-2-trifluoromethoxyphenyl | |
| 102 | O | F | 2-difluoromethoxy-3-chlorophenyl | |
| 103 | O | F | 2-difluoromethoxy-3-fluorophenyl | |
| 104 | O | F | 3-chloro-2-methoxyphenyl | |
| 105 | O | F | 2-methoxy-3-methylphenyl | |
| 106 | O | F | 2-propoxyphenyl | |

*The logP were determined in accordance with EEC Directive 79/831 Annex V. A8 by HPLC (gradient method, acetonitrile/0.1% aqueous phosphoric acid)

Preparation of a Starting Material of the Formula (III)

Example (III-1)

5,6-Difluoro-(3-fluorophenoxy)-pyrimidine 11.38 g (0.085 mol) of trifluoropyrimidine are dissolved in 240 ml of acetonitrile and admixed with 15.26 g (0.11 mol) of potassium carbonate, and the mixture is cooled to 10° C. Under argon, a solution of 9.52 g (0.085 mol) of 3-fluorophenol in 80 ml of acetonitrile is added dropwise. The mixture is then stirred under argon, without further cooling, for another 18 hours. The mixture is poured into 1 litre of water and extracted three times with in each case 150 ml of ethyl acetate, and the organic phase is dried over sodium sulphate and concentrated under reduced pressure. The residue is subjected to kugelrohr distillation. This gives 15.2 g (79.1% of theory) of 5,6-difluoro-(3-fluorophenoxy)-pyrimidine of boiling point 95° C. at 0.5 mbar.

Use Examples

Example A

Leptosphaeria Nodorum Test (Wheat)/Protective

| Solvent: | 25 parts by weight of N,N-dimethylacetamide |
|---|---|
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of 80%.

Evaluation is carried out 10 days after the inoculation. 0% means an efficacy which corresponds to that of the control, whereas an efficacy of 100% means that no infection is observed.

In this test, the substances according to the invention listed in Examples (6), (8) and (17) exhibit, at an application rate of 250 g/ha, an efficacy of 95% or more.

Example B

Phytophthora Test (Tomato)/Protective

| Solvent: | 24.5 parts by weight of acetone |
|---|---|
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

In this test, the substances according to the invention listed in Examples (3), (4), (7), (11) and (17) exhibit, at an application rate of 100 g/ha, an efficacy of 90% or more.

Example C

Plasmopara Test (Grapevine)/Protective

| | |
|---|---|
| Solvent: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substances according to the invention listed in Examples (4), (7), (11) and (17) exhibit, at an application rate of 100 g/ha, an efficacy of 95% or more.

Example D

Venturia Test (Apple)/Protective

| | |
|---|---|
| Solvent: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 12 days after the inoculation. 0% means an efficacy which corresponds to that of the control, whereas an efficacy of 100% means that no infection is observed.

In this test, the substances according to the invention listed in Examples (3), (4), (7), (11) and (17) exhibit, at an application rate of 10 g/ha, an efficacy of 90% or more.

Example E

Pyricularia Test (Rice)/Protective

| | |
|---|---|
| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound at the stated application rate. After the spray coating has dried on, the plants are inoculated with an aqueous spore suspension of *Pyricularia oryzae* and then remain at 100% relative atmospheric humidity and 26° C. for 24 h. The plants are then placed in a greenhouse at 80% relative atmospheric humidity and a temperature of 26° C.

Evaluation is carried out 7 days after the inoculation. 0% means an efficacy which corresponds to that of the control, whereas an efficacy of 100% means that no infection is observed.

In this test, the substances according to the invention listed in Examples (4), (6), (7), (8), (11) and (17) exhibit, at an application rate of 125 g/ha, an efficacy of 90% or more.

Example F

Sphaerotheca Test (Cucumber)/Protective

| | |
|---|---|
| Solvent: | 50 parts by weight of N,N-dimethylformamide |
| Emulsifier: | 1.17 parts by weight of alkylaryl polyglycol ether |

To produce a suitable preparation of active compound, 1 part by weight of active compound is mixed with the stated amounts of solvent, and the concentrate is diluted with water and the stated amount of emulsifier to the desired concentration.

To test for protective activity, young cucumber plants are sprayed with the preparation of active compound at the stated application rate. 1 day after the treatment, the plants are inoculated with an aqueous spore suspension of *Sphaerotheca fuliginea*. The plants are then placed in a greenhouse at a relative atmospheric humidity of 70% and a temperature of 23° C.

Evaluation is carried out 7 days after the inoculation. 0% means an efficacy which corresponds to that of the control, whereas an efficacy of 100% means that no infection is observed.

In this test, the substances according to the invention listed in Examples (4), (5), (7), (8), (9), (11) and (17) exhibit, at an application rate of 750 g/ha, an efficacy of 90% or more.

Example G

Plutella Test/Synthetic Feed

| Solvent: | 100 parts by weight of acetone |
| --- | --- |
| Emulsifier: | 1900 parts by weight of methanol |

To produce a suitable preparation of active compound, 1 part by weight of active compound is mixed with the stated amount of solvent, and the concentrate is diluted with methanol to the desired concentration.

A stated amount of the preparation of active compound of the desired concentration is pipetted onto a standardized amount of synthetic feed. After the methanol has evaporated, a film box lid covered with about 100 Plutella eggs is placed onto each cavity. The freshly hatched larvae migrate onto the treated synthetic feed.

After the desired period of time, the kill in % is determined. 100% means that all animals have been killed; 0% means that none of the animals have been killed.

In this test, for example, the following compound of the Preparation Examples exhibits good activity: (10).

What is claimed is:

1. A halogenopyrimidine of the formula (I)

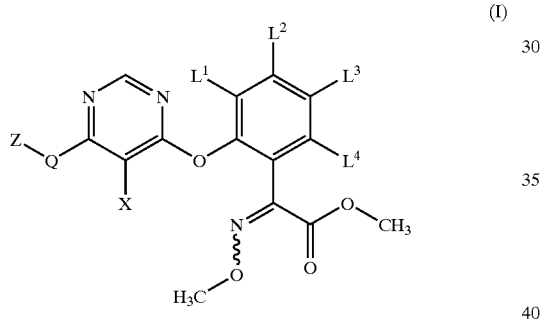

wherein

Z represents
  (i) cycloalkyl having 3 to 7 carbon atoms that is optionally mono- or disubstituted by halogen, alkyl or hydroxyl;
  (ii) heterocyclyl selected from the group consisting of thienyl, pyridyl, and furyl, each of which is optionally substituted by alkyl having 1 to 4 carbon atoms or halogen; or
  (iii) phenyl or naphthyl, each of which is optionally mono- to tetra-substituted by identical or different substituents, where the substituents are selected from the group consisting of halogen; cyano; nitro; amino; hydroxyl; formyl; carboxyl; carbamoyl; thiocarbamoyl; straight-chain or branched alkyl, hydroxyalkyl, oxoalkyl, alkoxy, alkoxyalkyl, alkylthioalkyl, dialkoxyalkyl, alkylthio, mercaptoalkyl, alkylsulphinyl, or alkylsulphonyl having in each case 1 to 8 carbon atoms; straight-chain or branched alkenyl or alkenyloxy having in each case 2 to 6 carbon atoms; straight-chain or branched halogenoalkyl, halogenoalkoxy, halogenoalkylthio, halogenoalkylsulphinyl, or halogenoalkylsulphonyl having in each case 1 to 6 carbon atoms and 1 to 13 identical or different halogen atoms; straight-chain or branched halogenoalkenyl or halogenoalkenyloxy having in each case 2 to 6 carbon atoms and 1 to 11 identical or different halogen atoms; straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl, or alkynylcarbonyl, having 1 to 6 carbon atoms in the respective hydrocarbon chains; cycloalkyl or cycloalkyloxy having in each case 3 to 6 carbon atoms; doubly attached alkylene having 3 or 4 carbon atoms, oxyalkylene having 2 or 3 carbon atoms, or dioxyalkylene having 1 or 2 carbon atoms, each of which is optionally mono- to tetrasubstituted by identical or different substituents selected from the group consisting of fluorine, chlorine, oxo, methyl, trifluoromethyl, and ethyl; a grouping

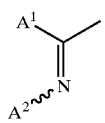

in which
  $A^1$ represents hydrogen, hydroxyl, alkyl having 1 to 4 carbon atoms, or cycloalkyl having 1 to 6 carbon atoms, and
  $A^2$ represents hydroxyl; amino; methylamino; phenyl; benzyl; optionally cyano-, hydroxyl-, alkoxy-, alkylthio-, alkylamino-, dialkylamino-, or phenyl-substituted alkyl or alkoxy having 1 to 4 carbon atoms; or alkenyloxy or alkynyloxy having in each case 2 to 4 carbon atoms; phenyl, phenoxy, phenylthio, benzoyl, benzoylethenyl, cinnamoyl, 1,3-dioxan-2-yl, benzimidazol-2-yl, dioxol-2-yl, oxadiazolyl, 2,3-dihydro-1,4-benzodioxin-6-yl, or benzo-dioxol4-yl, wherein each ring moiety is optionally mono- to trisubstituted by halogen and/or straight-chain or branched alkyl or alkoxy having 1 to 4 carbon atoms; and phenylalkyl, phenylalkyloxy, phenylalkylthio, 5,6-dihydro-1,4,2-dioxazin-3-ylmethyl, triazolylmethyl, or benzoxazol-2-ylmethyl, wherein the respective alkyl moieties have 1 to 3 carbon atoms and each ring moiety is optionally mono- to trisubstituted by halogen and/or straight-chain or branched alkyl or alkoxy having 1 to 4 carbon atoms;

Q represents oxygen or sulphur;

X represents fluorine, chlorine or bromine; and $L^1$, $L^2$, $L^3$, and $L^4$ are identical or different and independently of one another each represents hydrogen; halogen; cyano; nitro; or alkyl, alkoxy, alkylthio, alkylsulphinyl, or alkylsulphonyl having in each case 1 to 6 carbon atoms and being in each case optionally substituted by 1 to 5 halogen atoms.

2. A halogenopyrimidine of the formula (I) according to claim 1 wherein

Z represents
  (i) cyclopentyl or cyclohexyl, each of which is optionally mono- or disubstituted by fluorine, chlorine, methyl, ethyl, or hydroxyl;
  (ii) thienyl, pyridyl, or furyl, each of which is optionally substituted by methyl, ethyl or chlorine; or
  (iii) phenyl or naphthyl, each of which is optionally mono- to tetra-substituted by identical or different substituents, where the substituents are selected from the group consisting of fluorine; chlorine; bromine; iodine; cyano; nitro; amino; hydroxyl; formyl; carboxyl; carbamoyl; thiocarbamoyl; methyl; ethyl; n- or i-propyl; n-, i-, s-, or t-butyl; 1-, 2-, or 3-neopentyl; 1-, 2-, 3-, or 4-(2-methylbutyl); 1-, 2-, or 3-hexyl; 1-, 2-, 3-, 4-, or 5-(2-methylpentyl); 1-, 2-, or 3-(3-methylpentyl); 2-ethylbutyl; 1-, 3-, or 4-(2, 2-dimethylbutyl); 1- or 2-(2,3-dimethylbutyl); hydroxymethyl; hydroxyethyl; 3-oxobutyl; methoxymethyl; dimethoxymethyl; methoxy; ethoxy; n- or i-propoxy; methoxymethyl; ethoxymethyl; mercaptomethyl; methylthio; ethylthio; n- or i-propylthio; methylsulphinyl; ethylsulphinyl; methylsulphonyl; ethylsulphonyl; methylthiomethyl; ethylthiomethyl; vinyl; allyl; 2-methylallyl; propen-1-yl; crotonyl; propargyl; vinyloxy; allyloxy; 2-methylallyloxy; propen-1-yloxy; crotonyloxy; propargyloxy; trifluoromethyl; trifluoroethyl; difluoromethoxy; trifluoromethoxy; difluorochloromethoxy; trifluoroethoxy; difluoromethylthio; trifluoromethylth io; d ifluoroch loromethylthio; trifluoromethylsulphinyl; trifluoromethylsulphonyl; methylamino; ethylamino; n- or i-propylamino; dimethylamino; diethylamino; acetyl; propionyl; methoxycarbonyl; ethoxycarbonyl; methylaminocarbonyl; ethylaminocarbonyl; dimethylaminocarbonyl; diethylaminocarbonyl; dimethylaminocarbonyloxy; diethylaminocarbonyloxy; benzylaminocarbonyloxy; acryloyl; propioloyl; cyclopentyl; cyclohexyl; doubly attached propanediyl, ethyleneoxy, methylenedioxy, or ethylenedioxy, each of which is optionally mono- to tetra-substituted by identical or different substituents selected from the group consisting of fluorine, chlorine, oxo, methyl, and trifluoromethyl; a grouping

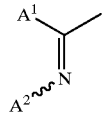

where
A¹ represents hydrogen, methyl, or hydroxyl, and
A² represents hydroxyl, methoxy, ethoxy, amino, methylamino, phenyl, benzyl, or hydroxyethyl; and phenyl, phenoxy, phenylthio, benzoyl, benzoylethenyl, cinnamoyl, benzyl, phenylethyl, phenylpropyl, benzyloxy, benzylthio, 5,6-dihydro-1,4,2-d ioxazin-3-ylmethyl, triazolylmethyl, benzoxazol-2-ylmethyl, 1,3-dioxan-2-yl, benzimidazol-2-yl, dioxol-2-yl, or oxadiazolyl, each of which is optionally mono- to tetrasubstituted in the ring moiety by halogen and/or straight-chain or branched alkyl or alkoxy having 1 to 4 carbon atoms;

Q represents oxygen;

X represents fluorine; and $L^1$, $L^2$, $L^3$, and $L^4$ are identical or different and independently of one another each represents hydrogen, methyl, ethyl, n- or i-propyl, or n-, i-, s-, or t-butyl.

3. A halogenopyrimidine of the formula (I) according to claim 1 in which Q represents oxygen.

4. A halogenopyrimidine of the formula (IV)

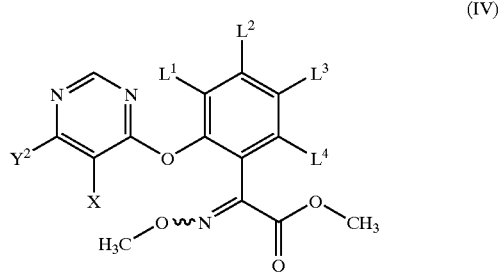

(IV)

in which

X, $L^1$, $L^2$, $L^3$, and $L^4$ are each as defined for formula (I) in claim 1, and $Y^2$ represents halogen.

5. A herbicidal composition comprising one or more compound of claim 1, and a member selected from the group consisting of extenders, carriers, surfactants and mixtures thereof.

6. A method for controlling undesirable plants comprising applying an effective amount of the compound of claim 1 to said undesirable plants and/or their habitat.

* * * * *